(12) United States Patent
Persson et al.

(10) Patent No.: US 10,176,372 B2
(45) Date of Patent: Jan. 8, 2019

(54) CLASSIFICATION OF MICROWAVE SCATTERING DATA

(75) Inventors: Mikael Persson, Alingsas (SE); Mohammad Ali Khorshidi, Solna (SE); Thomas Mckelvey, Alingsas (SE); Hamed Yousefi Mesri, Goteborg (SE); Masood Khazaeli Najafabadi, Goteborg (SE)

(73) Assignee: MEDFIELD DIAGNOSTICS AB, Gothenburg (SE)

( * ) Notice: Subject to any disclaimer, the term of this patent is extended or adjusted under 35 U.S.C. 154(b) by 1213 days.

(21) Appl. No.: 13/386,521

(22) PCT Filed: Jul. 23, 2010

(86) PCT No.: PCT/EP2010/060723
§ 371 (c)(1),
(2), (4) Date: Apr. 11, 2012

(87) PCT Pub. No.: WO2011/009945
PCT Pub. Date: Jan. 27, 2011

(65) Prior Publication Data
US 2012/0190977 A1    Jul. 26, 2012

Related U.S. Application Data

(60) Provisional application No. 61/227,870, filed on Jul. 23, 2009.

(51) Int. Cl.
*A61B 5/05* (2006.01)
*G06K 9/00* (2006.01)
(Continued)

(52) U.S. Cl.
CPC ........ *G06K 9/00536* (2013.01); *A61B 5/0507* (2013.01); *A61B 5/7267* (2013.01);
(Continued)

(58) Field of Classification Search
CPC ..... G01S 7/412; G01S 13/88; G06K 9/00536; G06K 9/6247; A61B 5/0507; A61B 2562/143
(Continued)

(56) References Cited

U.S. PATENT DOCUMENTS

| 6,454,711 B1 * | 9/2002 | Haddad et al. ................ 600/371 |
| 7,226,415 B2 * | 6/2007 | Haddad .................... A61B 5/05 600/371 |

(Continued)

FOREIGN PATENT DOCUMENTS

WO         9933399 A1    7/1999

OTHER PUBLICATIONS

H. Wang and N. Ahuja. Facial expression decomposition. In Proc. Ninth IEEE Int. Conf. on Computer Vision, vol. 2, pp. 958-965, Oct. 2003.*

(Continued)

*Primary Examiner* — Michael W Kahelin
*Assistant Examiner* — Helene Bor
(74) *Attorney, Agent, or Firm* — Young & Thompson

(57) ABSTRACT

Example embodiments presented herein relate to solutions for analyzing and/or classifying microwave scattering data. The analyzing and/or classifying may be utilized for estimating an internal condition in an enclosed volume.

16 Claims, 7 Drawing Sheets

(51) Int. Cl.
    *G06K 9/62*     (2006.01)
    *A61B 5/00*     (2006.01)
    *G01S 7/41*     (2006.01)
    *G01S 13/88*     (2006.01)

(52) U.S. Cl.
    CPC ............ *G01S 7/412* (2013.01); *G06K 9/6232* (2013.01); *G06K 9/6247* (2013.01); *A61B 2562/143* (2013.01); *G01S 13/88* (2013.01)

(58) Field of Classification Search
    USPC ........................................ 600/504, 430, 371
    See application file for complete search history.

(56) References Cited

U.S. PATENT DOCUMENTS

| | | | |
|---|---|---|---|
| 7,570,063 B2* | 8/2009 | Van Veen et al. | 324/637 |
| 2006/0050606 A1 | 3/2006 | Overthun et al. | |
| 2006/0115146 A1* | 6/2006 | Ogura et al. | 382/159 |
| 2008/0187174 A1* | 8/2008 | Metaxas | G06K 9/00335 382/103 |
| 2009/0238426 A1* | 9/2009 | Fear et al. | 382/128 |

OTHER PUBLICATIONS

Ferguson et al. "Identification of biological tissue using chirped probe THz imaging." Microelectronics Journal 33.12 (2002): 1043-1051.*

Dragana Veljkov C et al: "Extension of Mutual Subspace Method for Low Dimensional Feature Projection", Image Processing, 2007, IEEE International Conference, Sep. 1, 2007 (Sep. 1, 2007), pp. II-449, XP031157958.

Hans-Peter Kriegel et al: "A General Framework for Increasing the Robustness of PCA-Based Correlation Clustering Algorithms", Jul. 9, 2008 (Jul. 9, 2008), Scientific and Statistical Database Management; [Lecture Notes in Computer Science], pp. 418-435, XP019090803.

Riechers RG et al: "Microwave detection system for locating hemorrhage sites within the cranium and other regions", Dayton Section Symposium, 1998, The 15th Annual AESS/IEEE, May 14, 1998 (May 14, 1998), pp. 1-12, XP010293672.

Casimir A Kulikowski: "Pattern Recognition Approach to Medical Diagnosis", IEEE Transactions on Systems Science and Cybernetics, IEEE, US, vol. 1, No. 3, Jul. 1, 1970 (Jul. 1, 1970), pp. 173-178, XP011163447.

M. Hubert and S. Engelen: "Robust PCA and classification in biosciences", BIOI NFORMATI CS, vol. 20, No. 11, Feb. 26, 2004 (Feb. 26, 2004), pp. 1728-1736, XP002622495.

Filzmoser et al: "Outlier identification in high dimensions", Computational Statistics and Data Analysis, vol. 52. No. 3, Nov. 6, 2007 (Nov. 6, 2007), pp. 1694-1711, XP022331814.

Elaine A Ryan et al: "Breast tissue classification using x-ray scattering measurements and multivariate data analysis; Breast tissue classification using x-ray scattering and multivariate analysis", Physics in Medicine and Biology, vol. 52. No. 22, Nov. 21, 2007 (Nov. 21, 2007), pp. 6679-6696, XP020127252.

Hans-Peter Kriegel et al: "Outlier Detection in Axis-Parallel Subspaces of High Dimensional Data". Apr. 27, 2009 (Apr. 27, 2009). Advances in Knowledge Discovery and Data Mining, pp. 831-838, XP019116811.

Hans-Peter Kriegel et al.: "Clustering High-Dimensional Data: A Survey on Subspace Clustering. Pattern-Based Clustering and Correlation Clustering", ACM Transactions on Knowledge Discovery From Data (TKDD), Mar. 2009 (Mar. 2009). pp. 1:1-1:58. XP002622496.

International Search Report, dated Feb. 23, 2011, in Application No. PCT/EP2010/060723.

\* cited by examiner

CLASSIFICATION OF MICROWAVE SCATTERING DATA

CROSS REFERENCE OF RELATED APPLICATIONS

This application is a National Stage Application under 35 U.S.C. § 371 originating from PCT Application No. PCT/EP2010/060723, which was filed Jul. 23, 2010. PCT Application No. PCT/EP2010/060723 claims priority to U.S. Provisional Application No. 61/227,870, filed Jul. 23, 2009. All application mentioned above are incorporated herein by reference.

TECHNICAL FIELD

Example embodiments presented herein relate to the collection and analysis of microwave scattering data.

BACKGROUND

The diagnostics of enclosed volumes, for example medical patients, is typically performed with the use of imaging techniques such as Magnetic Resonance Imaging (MRI). Other techniques, such as Electroencephalography (EEG), involve the analysis of measurement data, involving electrical activity of the brain, to perform diagnostics.

The analysis and processing of signals from diagnostics measurements may be difficult if the data is complex and large in volume. Thus, there is a need for using proper analysis tools and methods in order to determine relevant data and obtain relevant results.

SUMMARY

It is therefore an object of the present invention to provide solutions for handling microwave scattering data and provide a more reliable result for interpretation of the data.

While typically not used in the field of diagnostics, electromagnetic waves may be useful for various applications which require diagnosis. Electromagnetic waves provide a non-invasive measurement deep into different types of test subjects. Such measurements may provide useful information that is otherwise invisible to the human eye.

Some example embodiments are directed towards a device, and method for using such device, for determining an internal condition of an enclosed volume. The device may comprise a communication port that may be configured to receive microwave scattering measurement data, which may be related to the enclosed volume. The device may also include a processing unit that may be configured to perform a linear or nonlinear mapping, or classification, of the microwave scattering measurement data with respect to a training data set. The processing unit may further be configured to estimate the internal condition based on the linear or nonlinear mapping, or classification. The processing unit may also be configured to estimate at least one internal condition over a period of time.

The processing unit may also be configured to project the microwave scattering measurement data on to a sub-space in which the training data set lies. The processing unit may also be configured to calculate a distance between the projected microwave scattering measurement data and the training data set within the sub-space, wherein the internal condition may be a function of the distance. The distance may be a linear or angular distance.

The enclosed volume may be a patient and the internal condition may be a medical condition. The enclosed volume may also be a tree and the internal condition may be tree health.

Some example embodiments may be directed towards a system for determining an internal condition of an enclosed volume. The system may comprise a measurement apparatus that may be configured transmit and receive microwave data. The system may also comprise a device, such as discussed above, that may be configured to receive the microwave data. The system may further comprise control electronics that may be configured to control communications between the device and measurement apparatus.

Some example embodiments may be directed towards a computer readable medium encoded with a computer program for determining an internal condition of an enclosed volume. The program may comprise machine readable instructions for receiving microwave scattering measurement data related to the enclosed volume. The program may also comprise machine readable instructions for executing a mapping of the microwave scattering measurement data with respect to a training data set and machine readable instructions for estimating the internal condition based on the mapping.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION

In the following description, for purposes of explanation and not limitation, specific details are set forth, such as particular components, elements, techniques, etc. in order to provide a thorough understanding of the example embodiments. However, it will be apparent to one skilled in the art that the example embodiments may be practiced in other manners that depart from these specific details. In other instances, detailed descriptions of well-known methods and elements are omitted so as not to obscure the description of the example embodiments.

Electromagnetic waves at microwave frequencies can be used to provide information of an internal condition inside structural entities, or enclosed volumes, due to differences in dielectric properties. Different types of structural entities may be in the form of a human or animal body, or any type of organic or inorganic body, or any other structural entity known in the art which may exhibit different dielectric properties in the presence of microwaves.

Introduction

Figure 1:
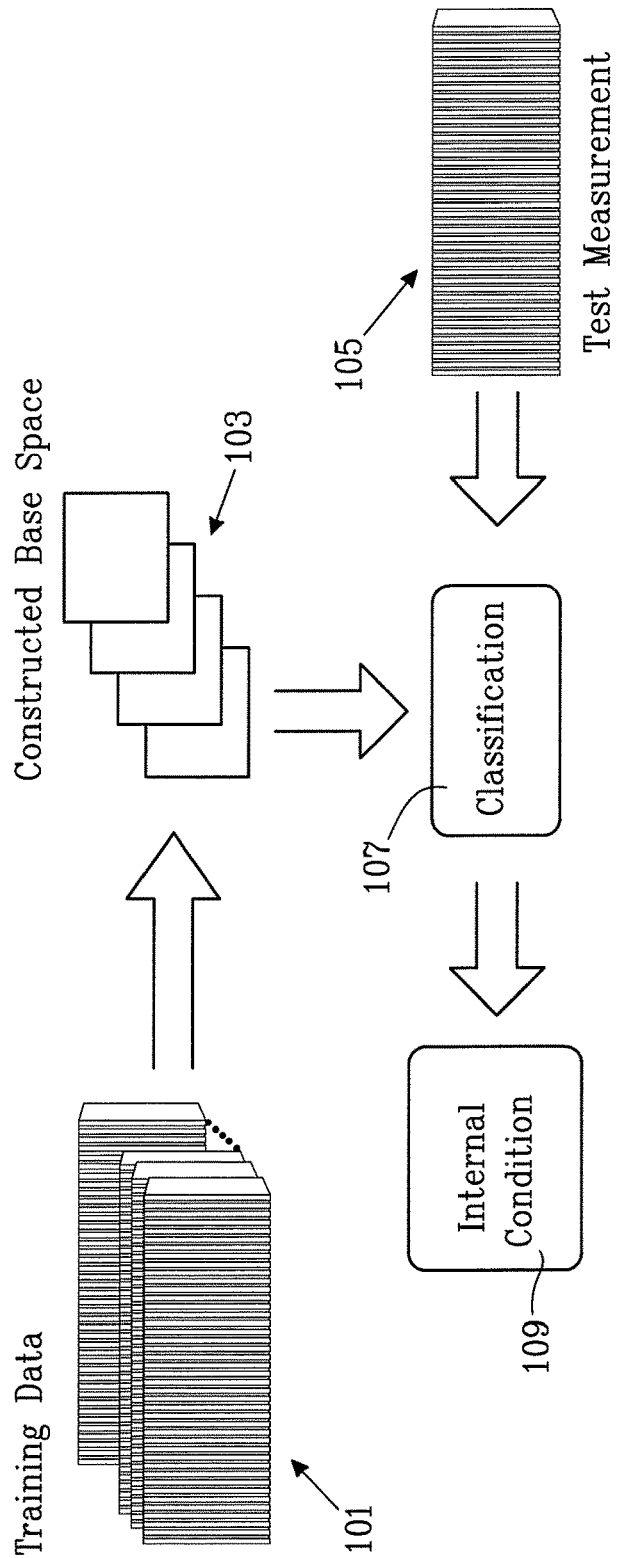
FIG. 1 illustrates a system overview of condition estimation using microwave scattering data, according to some example embodiments.
Figure 2:
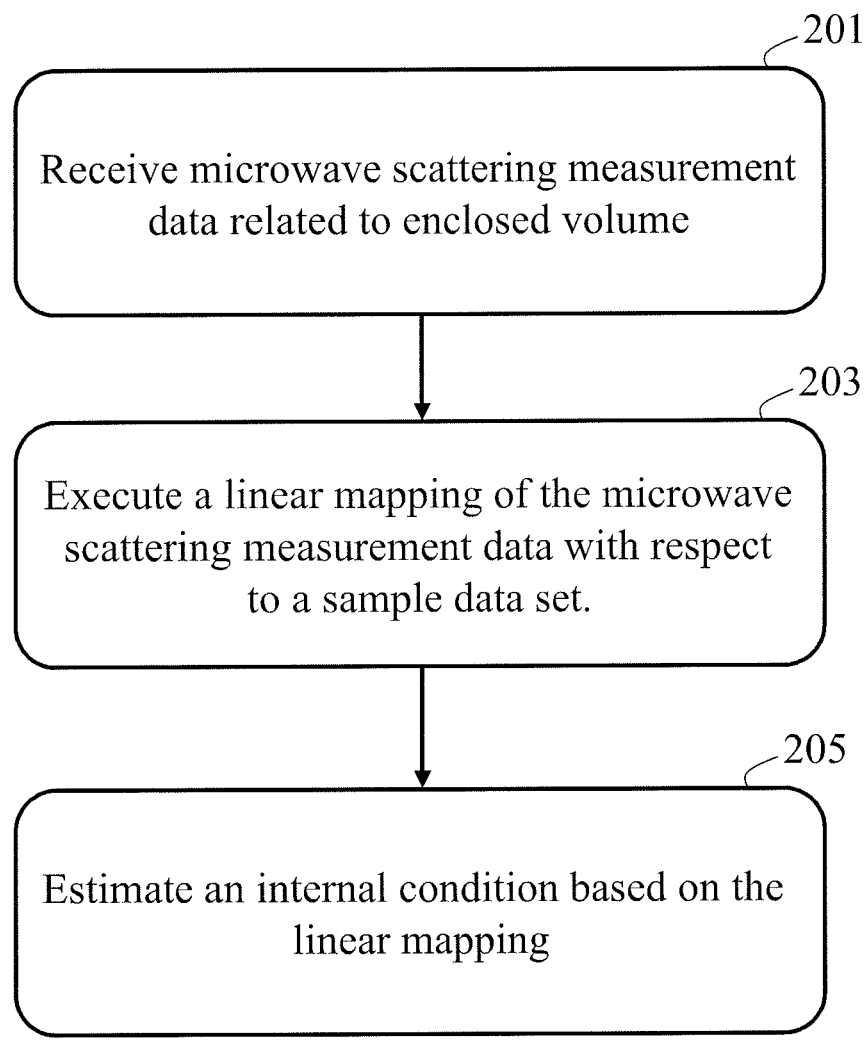
FIG. 2 is a flow diagram of example actions that may be taken by the system of FIG. 1, according to some example embodiments.

According to example embodiments, in providing information regarding an internal condition of an enclosed volume, a method and system for classification may be utilized. FIG. 1 provides an overview of such a system and FIG. 2 is a flow diagram depicting example actions to be taken by the system of FIG. 1.

First, a base space may be constructed with the use of training data 101. In some example embodiments, training data may comprise microwave scattering data from test subjects which are known to be healthy. Upon obtaining measurements from various training samples, the training data may be utilized in constructing the base space 103. Thereafter, the constructed base space 103 and a test measurement 105 may be input into a classifier 107. The received test measurement 105 may be in the form of microwave scattering data related to an enclosed volume whose internal condition is to be determined (201). The classifier 107 may execute a linear or nonlinear mapping of the test measurement 105 with respect to the constructed base space 103 (203). Based on this linear or nonlinear mapping, the classifier 107 may provide an estimated internal condition 109 (205).

Example embodiments described herein will be described in the following manner. First example embodiments directed towards the collection of scattered microwave data will be provided. Second, example embodiments of data analysis or classification with respect to Higher Order Singular Value Decomposition (HOSVD) and experimental results will be provided. Finally, example embodiments directed towards analysis or classification of data with respect to Subspace distancing and experimental results will be discussed.

Data Collection:

The following example embodiments relating to data collection will explained through the use of medical diagnostics. It should be appreciated that the use of medical diagnostics is merely an example application for the purpose of explanation. One of skill in the art would appreciate that example embodiments presented herein may be applied to any applications dealing with the collection of microwave data in relation to an internal status of a structural entity. It should further be appreciated that the manners of data collection discussed herein may be utilized for the collection of training data as well as test measurement data.

Electromagnetic waves at microwave frequencies can penetrate into the human, or animal, body. This property of microwave frequency signals makes it feasible to perform non-invasive measurements in order to detect changes or differences in subjects. It has been demonstrated that blood changes the dielectric properties of brain tissues. A clinically important application is to detect bleedings in the head, particularly in order to quickly discriminate a bleeding stroke from a stroke caused by clotting. Electromagnetic measurements may be used to detect various stroke types and discriminate between healthy and bleeding and/or clotting subjects by deriving useful features from the measurement data.

Figure 3A:
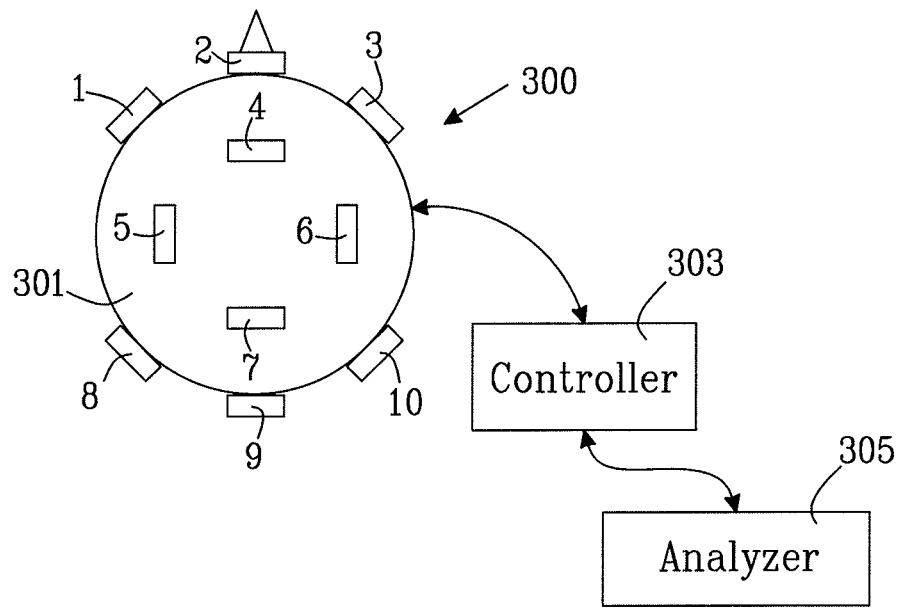
FIGS. 3A and 3B are block diagrams of a measurement apparatus that may be included in the system of FIG. 1, according to some example embodiments.
Figure 3B:
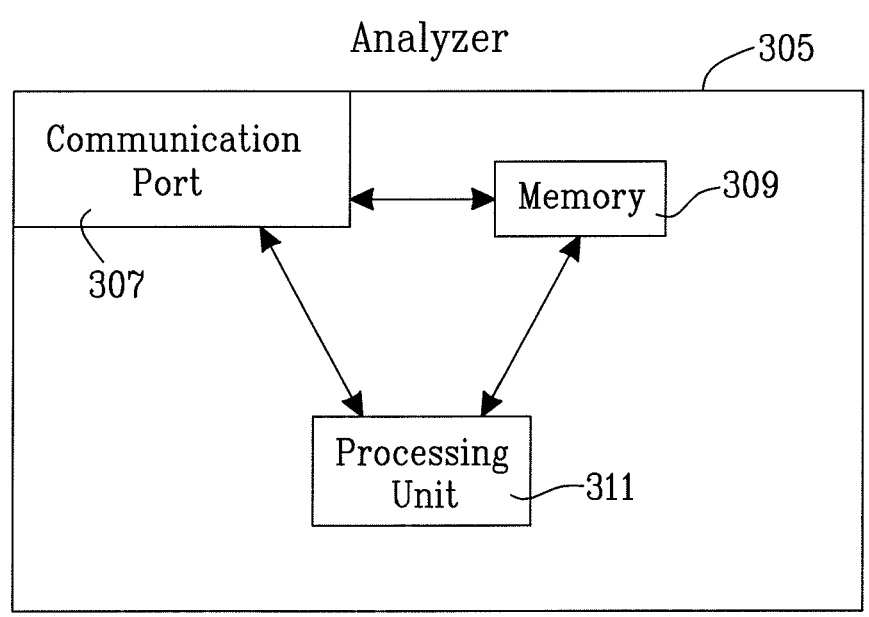

FIGS. 3A and 3B provide an example of a measurement device that may be utilized in the collection of electromagnetic measurement data. The measurement device of FIG. 3A may comprise an antenna array helmet 300 featuring a number of micro strip antennas, labeled 1 through 10, configured to be placed on a patient's head 301. The micro strip antennas of array helmet 300 may be fitted with V-shaped slots and a short circuit wall. Adjustable water containers may also be included between the antennas and the skull of the patient for impedance matching. It should be appreciated that while FIG. 3A illustrates the use of 10 antennas, any number of antennas, in any type of arrangement, may be utilized in the data collection.

The antenna array helmet 300 may be connected to a controller 303, which may in turn be connected to an analyzer 305. It should be appreciated that the various elements of FIG. 3A may be in connection via a wireless or wired connection, or any other means of component connection known in the art. It should further be appreciated that all the components of FIG. 3A may be integrated into a single device. In some example embodiments the analyzer 105 may be in the form of a Port Network Analyzer (PNA) and the controller 103 may be in the form of a switch module.

FIG. 3B illustrates example components which may be included in the analyzer 305. The analyzer 305 may include a communication port or any form of signal input/output interface 307 that may be configured to receive and/or transmit measurement data or an estimated condition. The communication port 307 may also be in communication with other devices in a network, e.g. with any device on a packet based network such as the Intranet, Ethernet, or other devices in a care facility. Example embodiments may for instance be used for transmitting a communication indicating an alarm to a central surveillance device or to a care personnel device.

The analyzer 305 may also include at least one memory unit 309 that may be configured to store measured data, constructed base spaces, executable program instructions, and/or estimated internal conditions. The memory unit 309 may be any suitable type of computer readable memory and may be of volatile and/or non-volatile type.

The analyzer 305 may further include a processing unit, or classifier, 311 that may be configured to provide the linear or nonlinear mapping, or classification, of the test measurement data with the constructed base space. The processing unit, or classifier, 311 may further be configured to provide an estimation of the internal condition based on the linear or nonlinear mapping. The processing unit, or classifier, 311 may be any suitable type of computation unit, e.g. a microprocessor, digital signal processor (DSP), field programmable gate array (FPGA), or application specific integrated circuit (ASIC).

In operation the various antennas 1 through 10 of the array helmet 300 may be configured to emit electromagnetic waves in a range of 100 MHz to 3 GHz with steps of 3 MHz. It should be appreciated that the frequency range and frequency step provided is merely an example and example embodiments may be applied with the use of other ranges and/or steps. As an example, the frequency range may be any range within 100 MHz to 3 GHz, or any other frequency range. As an example, the frequency steps may also be 1 MHz, 2 MHz, 4 MHz, 5 MHz, 6 MHz, 7 MHz, 8 MHz, etc. The analyzer 305 may be configured to perform measurements of reflection and transmission coefficients. The controller 303 may be configured to control connections and disconnections of the antennas 1 through 10 to the analyzer 305.

It should be appreciated that the components or system of FIGS. 3A and 3B may be configured to monitor the condition of a patient over a period of time, and/or the system may be configured to provide an instantaneous estimation of an internal condition. For long term monitoring, the system may be configured to monitor a patient and trigger levels may be set for controlling transmission of alarm signals to a care provider.

Data Formation—Higher Order Singular Value Decomposition (HOSVD):

In obtaining the measured training data utilized in the example embodiments directed towards HOSVD, the analyzer 305 may be configured to collect one reflection and one transmission coefficient at each time slot. Thus, measurements may be performed with fixed sending and receiving antennas for the entire operating frequency range and thereafter with the same sending antenna and next receiving antenna. Therefore, the measurement system has a multichannel setup with a single input and multiple output structure (SIMO).

Figure 4A:
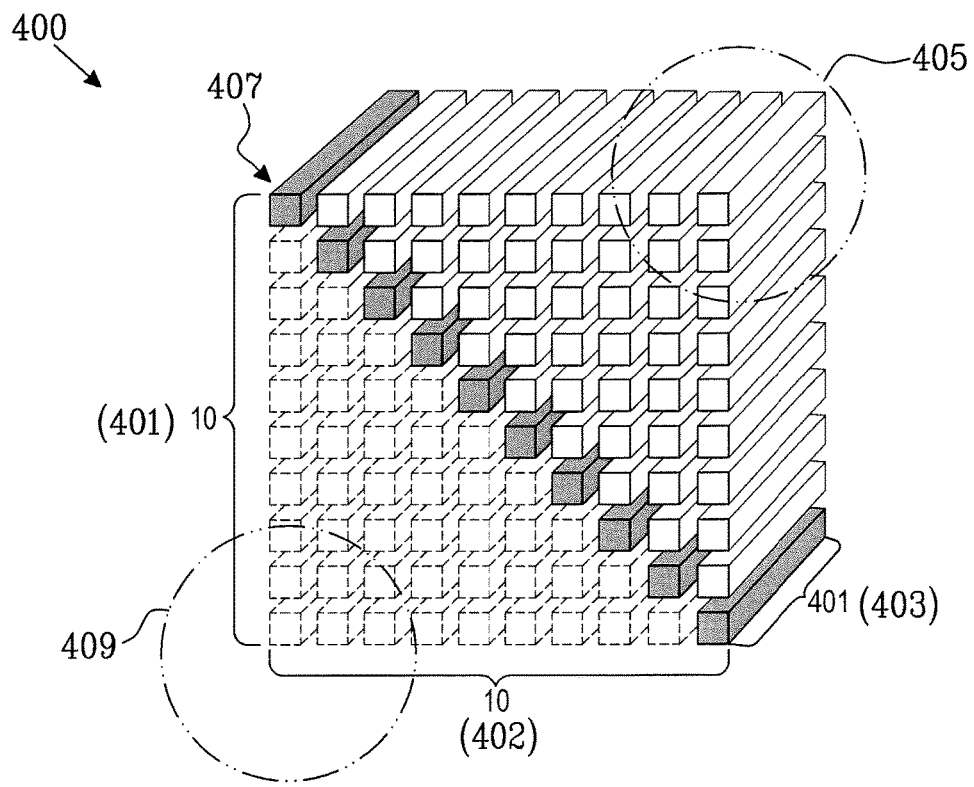
FIGS. 4A and 4B are illustrative examples of microwave scattering data formats, according to some example embodiments.

FIG. 4A provides a depiction of a training data measurement array 400 that may be obtained using the measurement device of FIGS. 3A and 3B, according to example embodiments involving HOSVD. The microwave training measurement data may be stored in a three dimensional complex tensor in which the 1st and 2nd dimensions, 401 and 402, may correspond to the sending and receiving antenna index, and the 3rd dimension 403 may correspond to wave frequencies utilized during a frequency sweep. In the example provided, the height 401 and width 402 of the array 400 may be defined by the number of antennas utilized in the measurement (10 antennas). While the depth 403 of the array 400 may be defined by the number of frequency steps utilized in the measurement (401 steps).

The data structure of FIG. 4A may comprise three different sections: (1) an upper triangular section 405, (2) a main diagonal section 407, and (3) a lower triangular section 409. The upper triangular section 405 may represent the transmission coefficients which correspond to the sending and receiving of electromagnetic waves with different antennas. The main diagonal section 407 may correspond to the reflection coefficients which are due to the sending and receiving of electromagnetic waves with the same antennas. The lower triangular section 409 may correspond to the transmission coefficients with reversed antenna indexes. It is theoretically proven that the transmission coefficients in both directions are the equal. Therefore, the lower triangular section 409 is the copy of the upper triangular section 405. Given this symmetry, multichannel signal processing techniques, according to example embodiments, may be used to restructure the training data into a two dimensional format as shown in FIG. 4B.

Figure 4B:
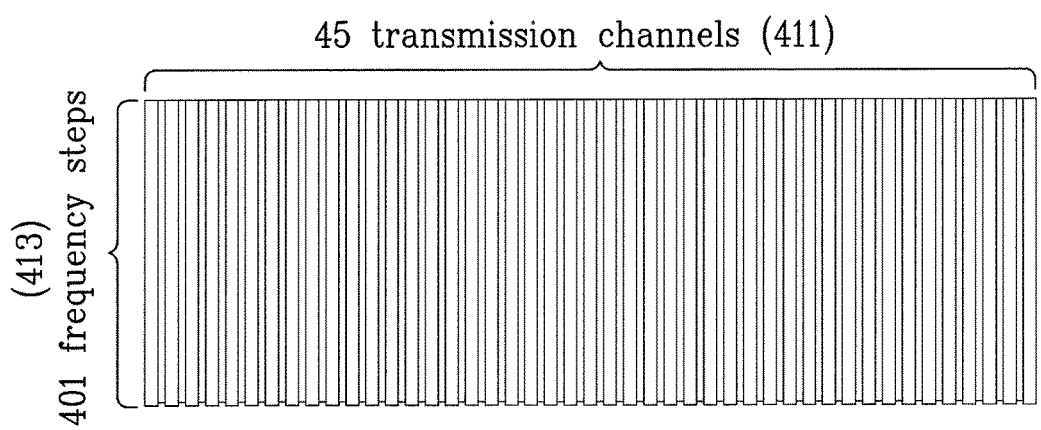

As shown in FIG. 4B, each training measurement may be reduced to a two dimensional matrix or array with the first dimension 411 representing the transmission channels where the number of transmission channels equals the total number of combinations of sending and receiving antennas (a total of 45 combinations for 10 antennas). The second dimension 413 represents the different wave frequencies (401 steps in the frequency sweep). Such a data format reduces the complexity of the base space construction, which may be utilized during classification and estimation.

In constructing the base space, HOSVD decomposition may be utilized on multiple sets of two dimensional training data sets, in which the individual measurement arrays may be arranged in a vertical manner according to information which is of most interest. In this example the information of most interest is channel information or measurement data. The resulting arrangement will provide information related to the frequency and measurement data of each reading of the frequency sweep. Thus, information relating to the different measurements may be obtained rather than the different channels or antennas used.

In providing the HOSVD constructed space, tensor decomposition may be used, according to some example embodiments. Generally, each Tensor may be written as a product:

$$\mathcal{D} \in \mathbb{C}^{I_1 \times I_2 \times \ldots \times I_N}$$

may be written as a product:

$$\mathcal{D} = S \times_1 U^{(1)} \times_2 U^{(2)} \times \ldots \times_N U^{(N)}$$

where $U^{(N)}$ are unitary $(I_N \times I_N)$ matrices. S is a complex tensor with the same dimension as D with the following properties: (1) every two subtensors and $S_{i=\alpha}$ and $S_{i=\beta}$ in the same mode are orthogonal when $\alpha \neq \beta$, and (2) the norms of the subtensors are ordered where:

$$\|S_{i=1}\| \geq \|S_{i=2}\| \geq \ldots \geq \|S_{i=n}\| \geq 0$$

By using HOSVD decompositioni, according to example embodiments, it is possible to write each tensor D as a sum of tensors, as illustrated in the following equation:

$$\mathcal{D} = \Sigma_{i=1}^{n_3} A_i \times_3 u_j^{(3)}$$

in which $A_i = S(:,:,i) \times_1 U^{(1)} \times_2 U^{(2)}$ are orthogonal bases. The constructed base space may comprise any number of the summed tensors.

Upon obtaining the HOSVD constructed space, post HOSVD classification may be performed in order to calculate an internal condition.

Post-Higher Order Singular Value Decomposition (HOSVD) Classification

In performing the classification to obtain an internal condition, the analyzer or classifier 305 may perform a classification comprising a linear or nonlinear mapping, or projection, of test data with respect to the constructed base space discussed above. Once the mapping is established, an angular deviation from a mean of healthy training samples included in the base space and the test measurement data may be calculated.

For each new test measurement 105 that is input to the analyzer or classifier 305, three measurements may be calculated. First, the deviation between the mean of the training data of the base space is calculated. Second, the angle between the deviation of the new test measurement from the mean of the training data 105 and the deviation space is calculated. Third, the angle between the training mean and the deviation space is calculated, which is referred to herein as $\theta_{AVRG}$.

Figure 5:
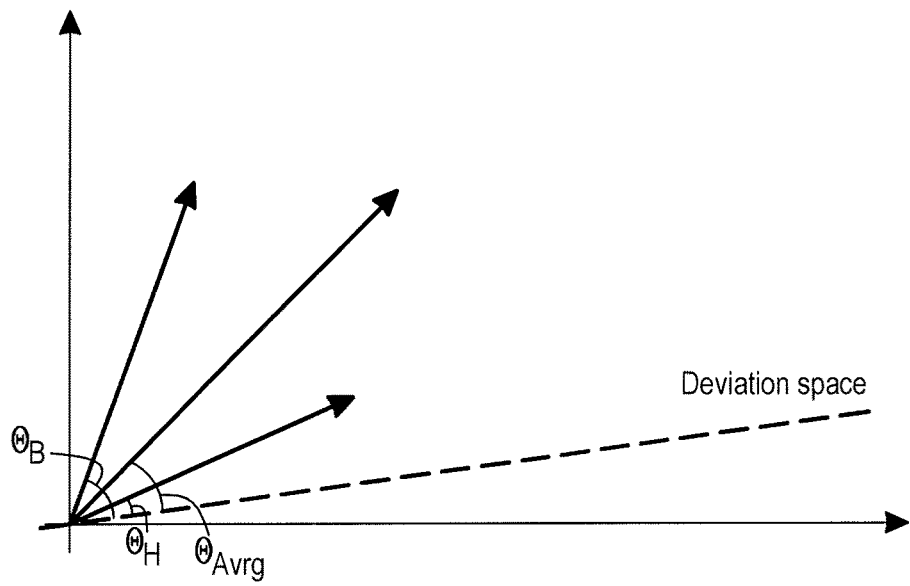
FIGS. 5 and 6 are illustrative examples of calculated angular distance, according to some example embodiments.

In some example embodiments, an internal condition of whether a patient has a bleeding stroke or is healthy may be provided using the angular data. As illustrated in FIG. 5, it was observed that for healthy subjects the difference of the angle between average $(\theta_{AVRG})$ and the new measurement was positive $(\theta_H)$, while for bleeding subjects this difference was negative $(\theta_B)$.

One example advantage of the HOSVD classifier is that there is no need to define a threshold value with respect to different bases. Therefore, as an example, the threshold value can be set to zero and negative angles will show the bleeding subject while positive angles with show the healthy samples.

It should be appreciated that classifications may be made between different conditions. For example, in addition to determining if a patient is a bleeding subject or a healthy subject, example embodiments may be used to determine if the patient has a clot. Thus, the example embodiments presented herein may be used to classify the patient in any number of categories or diagnoses.

Figure 6:
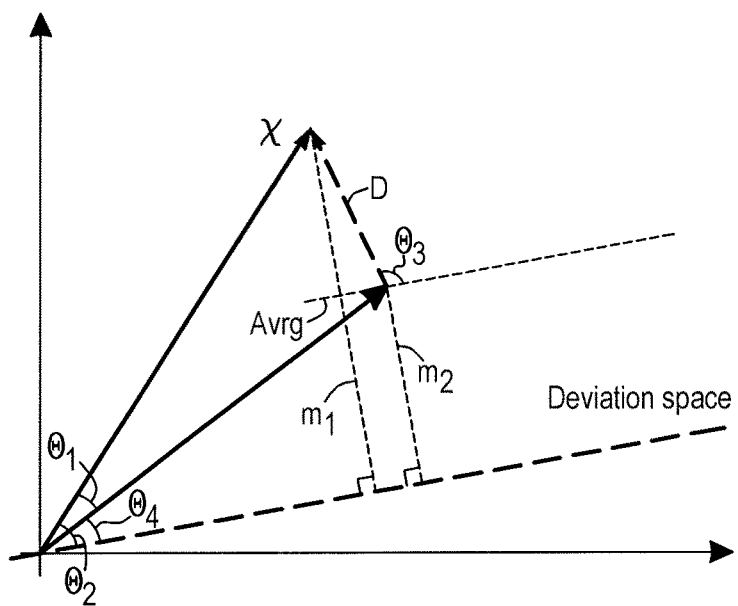

In one example embodiment, in order to perform further classification of the internal condition, additional measurement parameters may be defined. Examples of these additional features are shown in FIG. 6. The angle between each new test measurement and an average of the healthy training data may be represented by $\theta_1$. The normal of the new test measurement may be represented by $\|X\|$. The angle between the new test measurement and the deviation space is represented by $\theta_2$. The distance between the new test measurement and the deviation space is represented by $m_1$. The angle between a difference vector of the average of the healthy training data and the new test measurement may be represented by $\theta_3$. The normal of the difference vector is represented by $\|D\|$. The difference between the distance of the average of the healthy training data and the new test measurement is represented by $m_1$-$m_2$. Finally, the difference of the average angle and the new measurement is represented by $\theta_4$-$\theta_1$.

The extraction of multiple features of characteristics of the measurement data may be utilized by the analyzer, or classifier, to create a function which may be mapped to the constructed base space. The relationship between the various defined characteristics and base space may provide further information regarding the internal condition. It should be appreciated that any type and number of measurement characteristic may be utilized. Thus, by utilizing the extraction of multiple features, the internal condition estimation may yield more informative results.

Experimental Results—Higher Order Singular Value Decomposition (HOSVD)

In order to measure the performance of the experimental data some parameters have been defined. These parameters are Sensitivity, Specificity, Decision Boundary and Mean Difference.

Sensitivity is the probability that a bleeding subject is classified correctly as bleeding. On the other hand, Specificity is the probability that a healthy subject has been classified correctly as healthy. Decision Boundary is the difference between the maximum angle of bleeding samples and the minimum angle of healthy samples. The Decision Boundary provides information about the reliability of the example HOSVD embodiments and the safety margin. The Mean Difference is the difference of mean values for the healthy and bleeding distribution.

Figure 7:
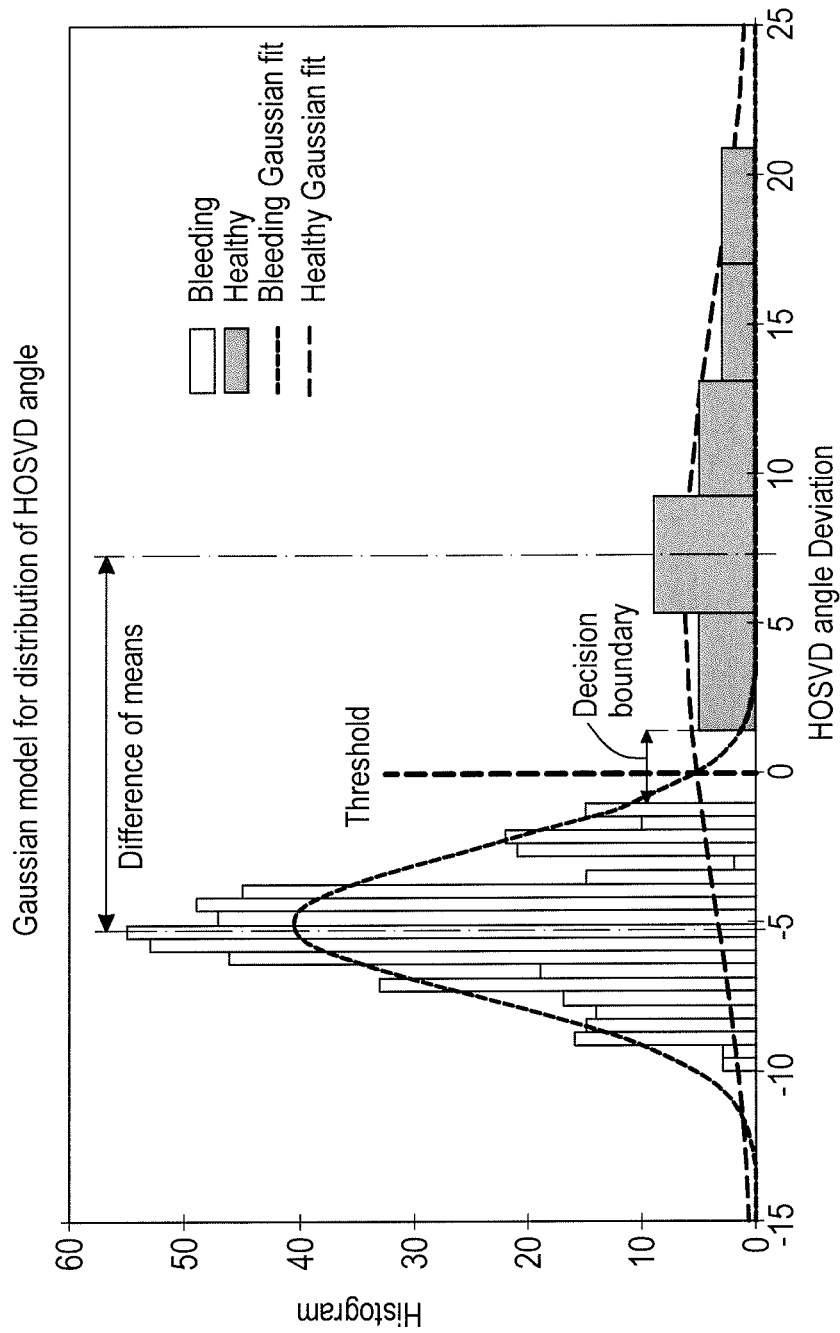
FIGS. 7, 8A, and 8B are graphical experimental results, according to some example embodiments.

The performance of the example embodiments has been evaluated for different frequency ranges and different data forms and the results indicate that the example embodiments work with no misclassification for bleeding subjects (100% sensitivity) as well as no misclassification for healthy subjects (100% specificity) as is depicted in FIG. 7.

FIG. 7 illustrates the distribution of the HOSVD angle for healthy and bleeding samples. As shown, the example embodiments presented herein may provide diagnostics with 100% sensitivity and 100% specificity. Furthermore, the distribution of angle is Gaussian for both healthy and bleeding subjects.

Experimental tests have also been performed on example embodiments which discriminate between bleeding and clotting patients, as illustrated in FIG. 6. Tables 1 through 3 provide information regarding percentages of correct classification or estimation. All of the data in Tables 1 through 3 was obtained using the extracted parameters highlighted in FIG. 6.

Table 1 illustrates the probability of correctly classifying the clotting subjects as clotting for the HOSVD classifier.

|  | C1 | C2 | C3 | C4 | C5 | C6 | C7 | C8 | C9 | C10 | C11 | C12 |
|---|---|---|---|---|---|---|---|---|---|---|---|---|
| First day | 97% | 79% | 100% | 40% | 100% | 100% | 80% | 4% | 72% | 87% | 45% | 9% |
| Second day | 100% | 93% | 98% | 100% | 95% | 90% | 3% | 32% | 78% | 78% | 76% | 51% |

The data shown in Table 1 was obtained by using a classification neural network with five layers.

Table 2 illustrates the probability of correctly classifying the bleeding subjects as bleeding with the HOSVD classifier.

|  | B1 | B2 | B3 | B4 | B5 | B6 | B7 | B8 | B9 | B10 |
|---|---|---|---|---|---|---|---|---|---|---|
| First day | 91% | 66% | 75% | 5% | 33% | 16% | 100% | 94% | 94% | 100% |
| Second day | 55% | 58% | 63% | 41% | 36% | 69% | 25% | 88% | 100% | 77% |

The data shown in Table 2 was also obtained using the classification neural network. It should be appreciated that various other forms of classification may be employed and the use of a neural network is not a necessary feature.

Table 3 illustrates an example of other classifiers which may be utilized.

|  | Neural Networks | Random Forest Tree | SVM | J48 Trees | Naive Bayesian |
|---|---|---|---|---|---|
| Correctly Classified Instances | 81% | 92% | 52% | 86% | 62% |

The classifiers used in the example provided by Table 3 are neural networks, random forest tree, support vector machine (SVM), J48 decision tree, and Naive Bayesian. As illustrated, different classifiers will yield results of different accuracy. It should further be appreciated that the accuracy of the estimated condition may also depend on the characteristics or parameters which are extracted from the measurement data.

Classificiation—Subspace Distance (SD)

In the Subspace distance embodiments, data may be obtained in the same manner as described in FIGS. 1 through 3B. The data obtained from a single patient may be in the form of an array. The combined data obtained from multiple patients may be in the form of a multidimensional array where the size of the matrix may be determined by the number of test samples multiplied by the number of different combinations of antennas.

In summary, a subspace may be constructed using a number of training measurements from healthy samples. Utilizing an analyzer or classifier 305 according to SD example embodiments an estimated internal condition may be provided where the classifier linearly maps, or projects, each new test measurement onto the constructed subspace. The estimated internal condition may be a function of a linear distance from the projected test measurement and a mean of the training data in the constructed subspace.

When applying microwave scattering measurements towards the use of diagnostics, it should be appreciated that the number of dimensions of the measured data may exceed the number of training samples available. The training samples may be referred to as a base space with a size of m+1.

The base data may describe the normal variation seen in the measurements from healthy test subjects. To detect deviations from this class, i.e. to detect bleedings patients, a weighted distance of the test point from the sample mean of the base class may be calculated. The distance of each test point from sample mean of base space can be written as:

$$d=[(x_t-\bar{x})^T \Psi (x_t-\bar{x})]^{1/2}$$

where $\Psi$ is a semidefinite symmetric weighting matrix and $$\bar{x} = \frac{1}{m+1} \sum_{i=1}^{m+1} x_i$$

is the sample mean of the m+1 training samples from the base space.

Consider the sample data matrix $$X=[x_1-\bar{x}, x_2-\bar{x} \ldots x_{m+1}-\bar{x}]$$

where each column comprises one sample of the base data centered around the sample mean. Since the sample data matrix is based on centered data it may be approximated to have maximally rank m.

A singular value decomposition of the matrix is $$X=USV^T$$

where U is an n-by-n orthonormal matrix whose columns form a set of orthogonal basis vectors for X. S is n-by-m+1 diagonal matrix that comprises the singular values of X on the diagonal, and V is m+1-by-m+1 orthonormal matrix. By partitioning the factors, we $$U = [\hat{U}_1 \ \hat{U}_2] \text{ and } S = \begin{bmatrix} \hat{S}_1 & 0 \\ & \vdots \\ 0 & \ldots & 0 \\ & \hat{S}_2 \end{bmatrix}$$

where $\hat{U}_1 \in \mathcal{R}^{n \times m}$ and $\hat{S}_1 \in \mathcal{R}^{m \times m}$ represent the m for the non-singular values where as is a zero matrix. Thus, for any data point $x_i$ from the base set there exists an $\alpha_i \in \mathcal{R}^m$ such that $$x_i = \bar{x} + \hat{U}_1 \alpha_i$$

where $\hat{U}_1$ is a basis that describes the space within the base data varies around the sample mean.

Any test point $x_t$ in the n-dimensional space may be decompose as $$x_t = \bar{x} + \hat{U}_1 \alpha + \hat{U}_2 \beta$$

where $\alpha \in \mathcal{R}_m$ and $\beta \in \mathcal{R}_{n-m}$.

The distance between the query point $x_t$ and the sample mean $\bar{x}$ of the training data can be calculated by different choices of the weighting matrix $\Psi$. According to example embodiments, the distance in the space perpendicular of the base space is utilized; this distance is herein referred to as the Subspace distance. It should be appreciated that the distance utilized need not be perfectly perpendicular but may be within a range close to 90°. The measured test point and mean value is projected onto the subspace and then the distance from the subspace is calculated. Thus the weighing matrix may be represented by $$\Psi_{SD} = \hat{U}_2 \hat{U}_2^T = I - \hat{U}_1 \hat{U}_1^T$$

For an arbitrary test point $x_t$ the Subspace distance (SD) yields $$d_{SD} = (\beta^T \beta)^{1/2}.$$

Experimental Results—Subspace Distance (SD)

Experimental tests were performed where microwave scattering data was used for discriminating between the bleeding stroke patients and healthy subjects. This data was obtained from transmission and reflection coefficients of an antenna array with 10 antennas (90 coefficients). Each coefficient is complex and was sampled in a frequency range between 100 MHz and 1 GHz. The real and complex parts of the complex coefficients, for all frequencies, were collected into one real valued long vector which represents one multi-variable measurement. First, the Subspace distance (SD) was evaluated on experimental data collected from a brain phantom. Then, the Euclidean distance, PIM distance, and SD distance was evaluated on clinical data, with the Euclidean and PIM distance being known in the art.

Eight different measurements were made on an empty brain phantom as a non-bleeding group. Then, four different sizes of bleeding phantoms from 1 ml to 10 ml were measured as a bleeding group. Validation was performed using a leave-one-out method in the base data set. Hence, for each test, seven of the data points in the base data were used to derive the sample mean and Singular Value Decomposition (SVD) of the covariance matrix, and 1 data point (the one left out) in the base space was used to calculate the distance in the base space group.

Figure 8A:
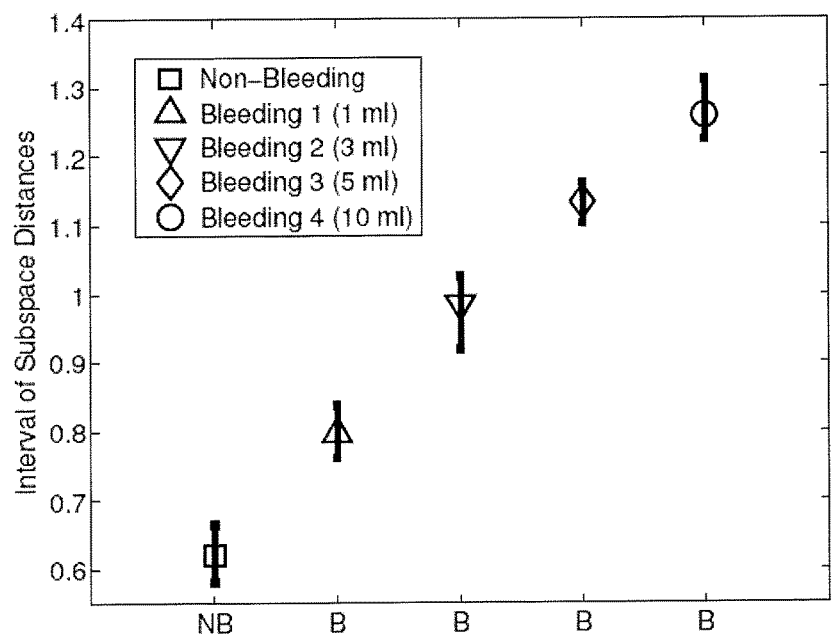

In FIG. 8A the results of the validation is presented in the form of bars indicating the maximum and minimum distance for all the eight test cases. From the graph, a threshold ($\eta$=0.7) can be identified between the bleeding (B) and non-bleeding (NB) subjects. Specifically, an internal condition estimation of bleeding (B) was provided for distances greater than 0.7. Thus, it can be seen that bleeding and non-bleeding subjects are separable by considering the Subspace distance. Another interesting result is that by increasing the bleeding size, the Subspace distance also increases monotonically. Thus, according to some example embodiments, the value of the Subspace distance may be correlated with the bleeding size.

In a second experimental test, measurements were made on both healthy subjects as well as patients with a diagnosed bleeding stroke. The data comprises of 35 non-bleeding, or healthy, samples and 16 samples measured from bleeding stroke patients. Again a leave-one-out validation method is made to assess the discriminating power between the three different distance measures.

Figure 8B:
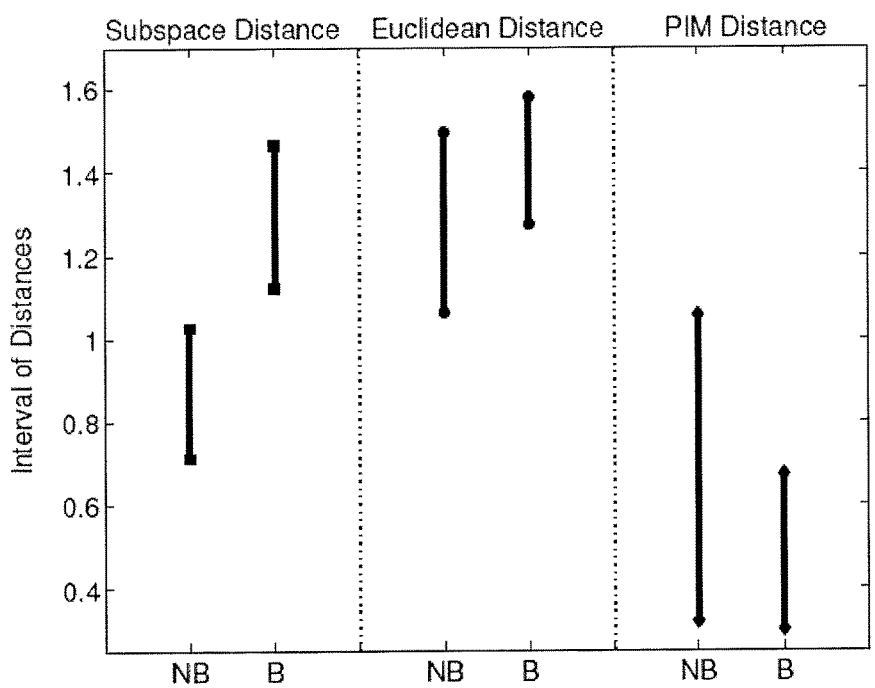

FIG. 8B illustrates the result of the clinical testing. The bars indicate the distance interval within the estimated bleeding (B) and non-bleeding (NB) internal conditions over the different leave-one-out validation runs when utilizing the Subspace distance, Euclidean distance, and the PIM distance. It is only the Subspace distance that can clearly separate the bleeding (B) group from the non-bleeding (NB)

group (i.e., there is no overlap between the estimated (B) and (NB) intervals). A threshold of η=1.1 could be defined for separating bleeding from non-bleeding subjects, where bleeding (B) estimations were obtained with Subspace distances of 1.1 or greater.

CONCLUSION

Example embodiments directed towards the estimation of an internal condition in an enclosed volume have been presented. A few example applications have been presented such as medical diagnosis for obtaining information about internal parts of human or animal body. However, one of skill in the art would appreciate that the example embodiments discussed may be used in any type of application utilizing microwave scattering data for the purpose of monitoring, detection, and/or diagnosis. For example, the embodiments presented herein may be utilized for various enclosed volumes such as trees, buildings, etc. Various different types of internal conditions may be monitored, for example, the presence of a particular liquid in the enclosed volume.

It should be noted that the word "comprising" does not exclude the presence of other elements or steps than those listed and the words "a" or "an" preceding an element do not exclude the presence of a plurality of such elements. It should further be noted that any reference signs do not limit the scope of the claims, and that several "means" or "units" may be represented by the same item of hardware.

The various embodiments of the present invention described herein is described in the general context of method steps or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), USB, Flash, HD, Blu-Ray, etc. Generally, program modules may include routines, programs, objects, components, data structures, etc. that performs particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A method of determining an internal condition of an enclosed volume that exhibits different dielectric properties in the presence of microwaves, the method comprising:
   using an array of transmitting antennas, emitting electromagnetic waves, wherein the emitting electromagnetic waves includes emitting microwaves, in steps over a frequency range, towards the enclosed volume, wherein the antennas are connected to a controller that is connected to an analyzer comprised of a classifier and a memory that stores measurement data;
   using receiving antennas, receiving electromagnetic waves scattered from the enclosed volume, the received electromagnetic waves containing microwave scattering measurement data related to said enclosed volume, wherein the receiving antennas are located in a fixed relationship to the array of transmitting antennas, wherein the microwave scattered electromagnetic waves are received in the steps over the frequency range and define an output signal;
   providing the output signal, in the steps over the frequency range, to the classifier;
   using the classifier to execute a mapping of the microwave scattering measurement data with respect to a training data set, wherein the training data set comprises microwave scattering measurement data from test subjects which are known to be healthy, wherein the executing further comprises projecting the microwave scattering measurement data onto a sub-space in which the training data set lies;
   using the classifier, estimating the internal condition based on the mapping, wherein the estimated internal condition is estimated as a function of a linear distance from the projected microwave scattering measurement data and the training data set within the sub-space, and the internal condition is a presence of a liquid in the enclosed volume,
   storing the training data set in the memory of the classifier in a matrix or array having a dimension which corresponds to at least one of the group consisting of a sending antenna index, a receiving antenna index, and wave frequencies utilized during a frequency sweep, wherein the training data set is stored a three dimensional complex tensor in which 1st and 2nd dimensions correspond to an sending antenna index and a receiving antenna index, and a 3rd dimension corresponds to wave frequencies utilized during a frequency sweep, and
   determining different dielectric properties of the enclosed volume, i) due to liquid changing the dielectric properties of the enclosed volume, and ii) using the stored training data set of the test subjects as the sub-space.

2. The method of claim 1 wherein an angular deviation from the training data set and the microwave scattering measurement data is calculated and used to the internal condition of the subject.

3. The method of claim 1 wherein the step of estimating further comprises estimating at least one internal condition over a period of time.

4. The method of claim 1 wherein the enclosed volume is a patient and the internal condition is a medical condition.

5. The method of claim 4, wherein the medical condition is healthy, bleeding stroke, and/or clotting stroke.

6. The method of claim 1, wherein,
   the controller controls connections and disconnections of the transmitting antennas and the receiving antennas to the analyser,
   the array of transmitting antennas is an array of antennas that, in operation, emit electromagnetic waves within a range of 100 MHz to 3 GHz,
   the array of antennas are within an array helmet,
   the enclosed volume is the patient's head, and
   during the emitting and receiving steps, the array helmet is placed on the patient's head.

7. The method of claim 1, wherein the enclosed volume is comprised of brain tissues, and the internal condition is a stroke condition which is one of the group consisting of a bleeding stroke and a clotting stroke.

8. The method of claim 1, wherein,
the classifier executes the step determining different dielectric properties of the first enclosed volume, i) due to blood changing the dielectric properties of the enclosed volume of the enclosed volume being a medical patient, and ii) the classifier performing linear or nonlinear mapping of the microwave scattering measurement data with respect to the stored training data set of the enclosed volume of the test subjects as the sub-space.

9. A device for determining an internal condition of an enclosed volume that exhibits different dielectric properties in the presence of microwaves, the device comprising:
an array of transmitting antennas that emit electromagnetic waves towards the enclosed volume, the emitted electromagnetic waves including microwaves emitted in steps over a frequency range;
receiving antennas located in a fixed relationship to the array of transmitting antennas that emit the electromagnetic waves including emitting microwaves;
a classifier;
a communication port configured to receive, using the receiving antennas, electromagnetic waves scattered from the enclosed volume, the received electromagnetic waves containing microwave scattering measurement data related to said enclosed volume, wherein the microwave scattered electromagnetic waves are received in the steps over the frequency range and define an output signal and used to provide an output signal, in the steps over the frequency range, to the classifier,
the classifier configured to receive the microwave scattered measurement data in the steps over the frequency range and execute a mapping of the microwave scattering measurement data with respect to a training data set, wherein the training data set comprises microwave scattering measurement data from test subjects which are known to be healthy,
wherein the classifier is further configured to project the microwave scattering measurement data onto a sub-space in which the training data set lies; and
the classifier further configured to estimate the internal condition based on the mapping, wherein the estimated internal condition is estimated as a function of a linear distance from the projected microwave scattering measurement data and the training data set within the sub-space, wherein the internal condition is a presence of a liquid in the enclosed volume,
wherein the classifier comprises a memory in which the training data set is stored in a matrix or array having a dimension which corresponds to at least one of the group consisting of a sending antenna index, a receiving antenna index, and wave frequencies utilized during a frequency sweep, the training data set is stored a three dimensional complex tensor in which 1st and 2nd dimensions correspond to an sending antenna index and a receiving antenna index, and a 3rd dimension corresponds to wave frequencies utilized during a frequency sweep, and
wherein the classifier is further configured determine different dielectric properties of the enclosed volume, i) due to liquid changing the dielectric properties of the enclosed volume, and ii) using the stored training data set of the test subjects as the sub-space.

10. The device of claim 9, wherein,
the array of antennas is an array of antennas that, in operation, emit electromagnetic waves within a range of 100 MHz to 3 GHz in steps over the range.

11. The device of claim 10, wherein,
the array of antennas are within a array helmet, and the array helmet is configured for placement on a patient's head such that the enclosed volume is the patient's head, and
the classifier is further configured to calculate a distance between the projected microwave scattering measurement data and the training data set within the sub-space, wherein the internal condition is a function of the distance.

12. The device of claim 10 wherein the distance is a subspace distance.

13. The device of claim 10 wherein subspace is a Higher Order Singular Value Decomposition (HOSVD) constructed subspace and the distance is an angular distance.

14. The device of claim 9 wherein the processing unit is further configured to estimate at least one internal condition over a period of time.

15. A non-transitory computer readable product encoded with a computer program for determining an internal condition of an enclosed volume that exhibits different dielectric properties in the presence of microwaves, the program comprising:
machine readable instructions for having an array of transmitting antennas emit electromagnetic waves including emitting microwaves, in steps over a frequency range, towards the enclosed volume, wherein the antennas are connected to a controller that is connected to an analyzer comprised of a classifier and a memory that stores measurement data;
machine readable instructions for having receiving antennas receive electromagnetic waves scattered from the enclosed volume, the received electromagnetic waves containing microwave scattering measurement data related to said enclosed volume, wherein the receiving antennas are located in a fixed relationship to the array of transmitting antennas, wherein the microwave scattered electromagnetic waves are received in the steps over the frequency range and define an output signal;
machine readable instructions for providing the output signal, in the steps over the frequency range, to the classifier;
machine readable instructions for executing a mapping of the microwave scattering measurement data with respect to a training data set, wherein the training data set comprises microwave scattering measurement data from test subjects which are known to be healthy, and wherein the executing further comprises projecting the microwave scattering measurement data onto a sub-space in which the training data set lies; and
machine readable instructions for estimating the internal condition based on the mapping, wherein the estimated internal condition is estimated as a function of a linear distance from the projected microwave scattering measurement data and the training data set within the sub-space, and the internal condition is a presence of a liquid in the enclosed volume,
machine readable instructions for storing the training data set in the memory of the classifier in a matrix or array having a dimension which corresponds to at least one of the group consisting of a sending antenna index, a receiving antenna index, and wave frequencies utilized during a frequency sweep, wherein the training data set is stored a three dimensional complex tensor in which 1st and 2nd dimensions correspond to an sending antenna index and a receiving antenna index, and a 3rd dimension corresponds to wave frequencies utilized during a frequency sweep, and machine readable instructions for determining different dielectric properties of the enclosed volume, i) due to liquid changing the dielectric properties of the enclosed volume, and ii) using the stored training data set of the test subjects as the sub-space.

16. The method of claim 1, wherein in said estimating the internal condition based on the mapping, the classifier calculates a linear distance between the projected microwave scattering measurement data and the training data set within the sub-space, wherein the internal condition is a function of the linear distance.

* * * * *